(12) United States Patent
Hansson et al.

(10) Patent No.: US 8,586,820 B2
(45) Date of Patent: Nov. 19, 2013

(54) ABSORBENT ARTICLE WITH COLOUR CHANGING PROPERTIES

(75) Inventors: Morgan Hansson, Göteborg (SE); Robert Torstensson, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 802 days.

(21) Appl. No.: 12/064,217

(22) PCT Filed: Sep. 13, 2005

(86) PCT No.: PCT/SE2005/001322
§ 371 (c)(1),
(2), (4) Date: Feb. 19, 2008

(87) PCT Pub. No.: WO2007/032711
PCT Pub. Date: Mar. 22, 2007

(65) Prior Publication Data
US 2008/0234644 A1    Sep. 25, 2008

(51) Int. Cl.
*A61F 13/15* (2006.01)
(52) U.S. Cl.
USPC .......................................................... 604/361
(58) Field of Classification Search
USPC .......................................................... 604/361
See application file for complete search history.

(56) References Cited

U.S. PATENT DOCUMENTS

| 4,681,791 | A | * | 7/1987 | Shibahashi et al. | 428/96 |
| 4,826,550 | A | | 5/1989 | Shimizu et al. | |
| 5,167,652 | A | | 12/1992 | Mueller | |
| 5,197,958 | A | | 3/1993 | Howell | |
| 5,298,035 | A | * | 3/1994 | Okamoto | 8/554 |
| 6,521,811 | B1 | * | 2/2003 | Lassen et al. | 604/378 |
| 6,749,935 | B2 | * | 6/2004 | Ishimura | 428/370 |
| 6,921,393 | B2 | * | 7/2005 | Tears et al. | 604/385.04 |
| 7,105,715 | B2 | * | 9/2006 | Carlucci et al. | 604/361 |
| 2002/0049418 | A1 | * | 4/2002 | London Brown | 604/367 |

(Continued)

FOREIGN PATENT DOCUMENTS

EP    0 347 657 A2    12/1989
EP    1 035 818 B1    9/2000

(Continued)

OTHER PUBLICATIONS

Form PCT/ISA/210 (International Search Report) dated Mar. 10, 2006.

(Continued)

*Primary Examiner* — Lynne Anderson
(74) *Attorney, Agent, or Firm* — Buchanan Ingersoll & Rooney PC

(57) ABSTRACT

An absorbent article such as a diaper, a pant diaper, a sanitary napkin, an incontinence guard etc., which includes thermochromic fibers. The thermochromic fibers may be incorporated in one or more of the following components of the absorbent article: the inner coversheet, the acquisition layer, the absorbent structure, the outer coversheet or a layer arranged between the outer coversheet and the absorbent structure. The article may alternatively contain a fibrous layer which mainly or entirely contains thermochromic fibers. The thermochromic fibers may be used as wetness indicator, as a fever indicator, as a function control for microorganisms that have been incorporated in the article or for amusement purposes, such as creating color imprints of hands etc.

16 Claims, 3 Drawing Sheets

(56) References Cited

U.S. PATENT DOCUMENTS

| | | |
|---|---|---|
| 2002/0090510 A1 | 7/2002 | Ono et al. |
| 2003/0014025 A1* | 1/2003 | Allen et al. ............ 604/361 |
| 2003/0087566 A1 | 5/2003 | Carlyle et al. |
| 2003/0114809 A1* | 6/2003 | Gagliardi et al. ......... 604/361 |
| 2004/0087922 A1 | 5/2004 | Bobadilla |
| 2005/0256479 A1 | 11/2005 | Carlucci et al. |
| 2008/0269704 A1* | 10/2008 | Hansson et al. ......... 604/366 |

FOREIGN PATENT DOCUMENTS

| | | |
|---|---|---|
| EP | 1 314 802 B1 | 5/2003 |
| EP | 1 591 131 A1 | 11/2005 |
| JP | 3-161511 A | 7/1991 |
| JP | 4-241115 A | 8/1992 |
| JP | 8-027653 A | 1/1996 |
| JP | 2001-055623 A | 2/2001 |
| JP | 2001-123088 A | 5/2001 |
| JP | 2002-138322 A | 5/2002 |
| WO | WO 03/035948 A1 | 5/2003 |
| WO | WO 2005/122984 A1 | 12/2005 |

OTHER PUBLICATIONS

Form PCT/ISA/237 (Written Opinion of the International Searching Authority) dated Mar. 10, 2006.
Form PCT/IPEA/409 (International Preliminary Report on Patentability) dated Sep. 6, 2007.
European Search Report issued on Jul. 22, 2011 by the European Patent Office in corresponding European Patent Application No. 05 77 7950.
Office Action issued in corresponding Columbian Patent Application No. 08.036.817, Dec. 20, 2011.

* cited by examiner

ABSORBENT ARTICLE WITH COLOUR CHANGING PROPERTIES

TECHNICAL FIELD

The present invention refers to an absorbent hygiene article such as a diaper, a pant diaper, a sanitary napkin, an incontinence guard etc. having colour changing properties at a selected temperature.

BACKGROUND

The concept of indicating wetness in an absorbent article, especially a diaper, by a wetness indicator, which by a colour change indicates the presence of body fluid in the diaper, is previously known.

Thus a wetness indicating diaper is known through U.S. Pat. No. 5,197,958 provided by printing a pattern by a thermochromic ink on the exterior surface of the outer coversheet of a diaper. This pattern of thermochromic ink becomes visible or changes colour when a selected temperature is exceeded, adapted to indicate that the diaper has been wetted by body fluid.

EP-A-0 347 657 discloses a wetness indicating hot-melt adhesive which changes colour in response to the presence of moisture. The hot-melt adhesive contains particles of a dyestuff which is insoluble in the adhesive composition, but which are soluble in water. The hot-melt adhesive can be used in a diaper as a wetness indicator.

U.S. Pat. No. 5,167,652 discloses a moisture sensitive film produced by blending a copolyester with a moisture absorbing copolyamide. The film turns white when wetted. The film may be used as a diaper backsheet to indicate when the diaper has been wetted.

There is however a continuing need for improvement and for more sophisticated ways of indicating an increase or decrease in temperature in an absorbent article above a selected threshold value, for example in order to indicate the presence of body fluid, to indicate fever of the wearer or for visual and to enhance the customer product perception. Alternatively it may be desired to make a welding pattern more visible by means of a differing colour.

OBJECT AND SUMMARY

An object of the present invention is to provide a solution to the problems set out above and to suggest an absorbent article having colour changing properties with a high degree of flexibility when it comes to the choice of where and how the colour changing means is placed in the article. The process of incorporating the colour changing means in the article should further be simple. These and further objects have been solved by the fact that that said absorbent article comprises thermochromic fibres.

The thermochromic fibres may be incorporated in different parts and components of the article. Thus in one aspect they are incorporated in the outer coversheet and/or a layer arranged between the outer coversheet and the absorbent structure.

According to one embodiment the outer coversheet comprises a fibrous layer containing at least 1% by weight, preferably at least 5%, more preferably at least 10% by weight and most preferably from 20 to 70% by weight, of said colour changing fibres, based on the weight of said fibrous layer in areas in which said thermochromic fibres are distributed. Thus if the thermochromic fibres are distributed in only in a limited area of a layer, the above concentrations should be calculated only on this limited area.

An entire layer may also consist of thermochromic fibres as the sole fibrous material, in which case the basis weight of such a layer should be at least 10 g/m$^2$, preferably at least 15 g/m$^2$.

Depending on what colour is used different amounts of thermochromic fibres in the layer may be used. For example for a yellow colour a higher amount of thermochromic fibres may be needed than for a black colour. In general the amount of thermochromic fibres should be sufficient to indicate a colour change.

In a further embodiment the fibrous layer containing the thermochromic fibres forms the external garment facing side of the outer coversheet.

In a still further embodiment the absorbent structure contains thermochromic fibres. According to one aspect the absorbent structure comprises at least 1% by weight, preferably at least 10% by weight and more preferably at least 20% by weight, of said thermochromic fibres, based on the total weight of said absorbent structure in areas in which said thermochromic fibres are distributed.

In a further aspect the absorbent article comprises a liquid pervious bodyside liner which contains thermochromic fibres.

In a still further aspect the article further comprises a liquid acquisition layer placed between the bodyside liner and the absorbent structure, wherein said acquisition layer contains thermochromic fibres.

In one embodiment the thermochromic fibres change colour at a temperature of between 25 and 43° C., preferably between 30 and 38° C.

In a further embodiment the article comprises at least two different types of thermochromic fibres having different colours and/or different trigger temperatures.

The disclosure further refers to the use of thermochromic fibres as a wetness indicator in an absorbent article. In this case it is preferred that the thermochromic fibres are incorporated in one or more of the following components of the absorbent article: the absorbent structure, the outer coversheet, a layer arranged between the outer coversheet and the absorbent structure and an acquisition layer.

Thermochromic fibres may further be used to enhance the customer product perception, and to increase the interaction between the user and the product, such as give play and learn features. One example would be to create colour imprints of hands etc. in an absorbent article. In this case the thermochromic fibres are incorporated in the outer coversheet of a diaper or pant diaper.

In a further embodiment thermochromic fibres are used as a fever indicator of a wearer of an absorbent article, wherein the thermochromic fibres are incorporated in one or more of the following components of the absorbent article: the inner coversheet, the acquisition layer and the absorbent structure.

In another aspect thermochromic fibres are used as a function control of microorganisms, for example *Lactobacillus*, added to an absorbent article, wherein the thermochromic fibres are incorporated in one or more of the following components of the absorbent article: the inner coversheet, the acquisition layer and the absorbent structure. The thermochromic fibres should in this case change colour at a temperature of at least 40° C., preferably at least 50° C. The change of colour should be irreversible.

In a further embodiment thermochromic fibres are contained in an elastic material, for example an elastic laminate which in some parts has bee de-elastified by heat treatment, ultrasonic welding or the like.

BRIEF DESCRIPTION OF DRAWINGS

The invention will be described in the following in greater detail by way of examples and with reference to the accompanying drawings, in which.

DEFINITIONS

Absorbent Article

Figure 1:
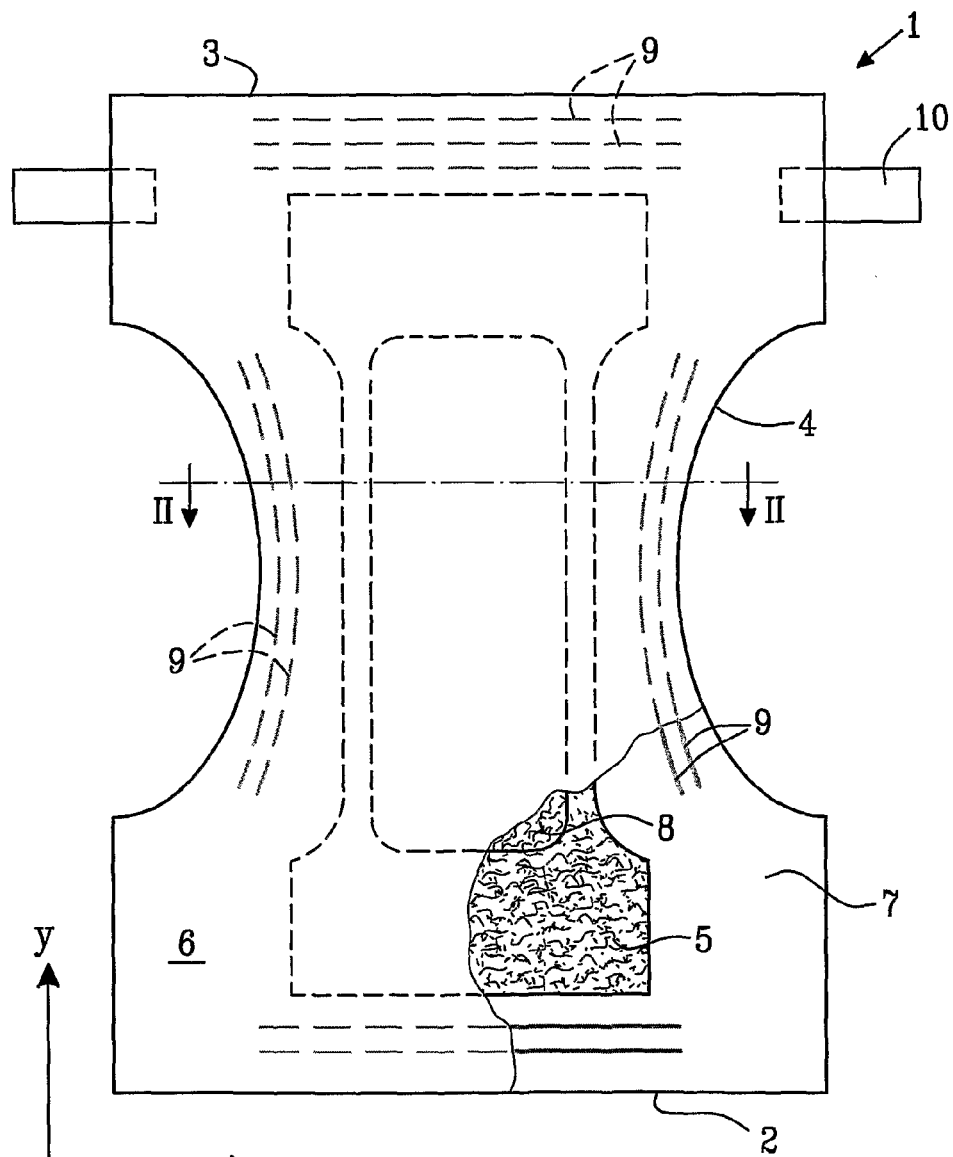
FIG. 1 is a schematic perspective view of a diaper.
Figure 2:
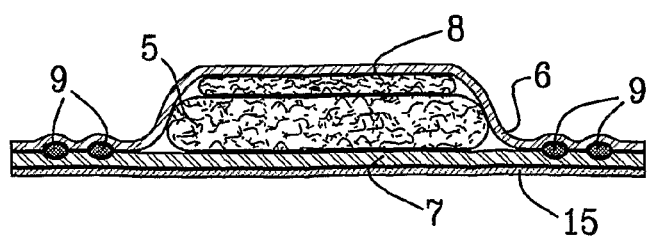
FIG. 2 is a section according to the line II-II in FIG. 1.

The term "absorbent article" refers to products that are placed against the skin of the wearer to absorb and contain body exudates, like urine, feces and menstrual fluid. The disclosure mainly refers to disposable absorbent articles, which are articles that are not intended to be laundered or otherwise restored or reused as an absorbent article after use.

Inner Liquid Permeable Cover

The inner liquid permeable cover forms the inner cover of the absorbent article and in use is placed in direct contact with the skin of the wearer. The inner liquid permeable cover can comprise a nonwoven material, e.g. spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The inner liquid permeable cover material may further be composed of tow fibres, which may be bonded to each other in a bonding pattern, as e.g. disclosed in EP-A-1 035 818. Further examples of inner liquid permeable cover materials are porous foams, apertured plastic films, laminates of film/nonwovens etc. The materials suited as inner liquid permeable cover materials should be soft and non-irritating to the skin and be readily penetrated by body fluid, e.g. urine or menstrual fluid. The inner liquid permeable cover may further be different in different parts of the absorbent article.

Outer Liquid Impermeable Cover

The outer liquid impermeable cover forms the outer cover of the absorbent article at least on the core area thereof. The outer liquid impermeable cover can comprise a thin plastic film, e.g. a polyethylene or polypropylene film, a nonwoven material coated with a liquid impervious material, a hydrophobic nonwoven material, which resists liquid penetration, or a laminate, e.g. of a plastic film and a nonwoven material. The outer liquid impermeable cover material may be breathable so as to allow vapour to escape from the absorbent structure, while still preventing liquids from passing through. Examples of breathable outer liquid impermeable cover materials are porous polymeric films, nonwoven laminates from spunbond and meltblown layers, laminates from porous polymeric films and nonwoven materials.

Absorbent Structure

The "absorbent structure" is the absorbent structure disposed between the two covers of the absorbent article. The absorbent structure can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent structure. Superabsorbent polymers are waterswellable, water-insoluble organic or inorganic materials capable of absorbing at least about 20 times its weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent structure comprising a matrix of hydrophilic fibers, such as cellulosic fibers, and superabsorbent material, the proportion of superabsorbent material is preferably between 10 and 90% by weight, more preferably between 30 and 70% by weight.

It is conventional in absorbent articles to have absorbent structures comprising layers of different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent polymers. The size and absorbent capacity of the absorbent structure may be varied to be suited for different uses such as for infants or for adult incontinent persons.

Acquisition Layer

A so called acquisition layer may be arranged between the inner liquid permeable cover and the absorbent structure. The acquisition layer is adapted to quickly receive and temporarily store discharged liquid before it is absorbed by the underlying absorbent structure. Such acquisition distribution layers are well known in the art and may be composed of porous fibrous waddings or foam materials.

Themochromic Fibres

Thermochromic pigments are organic compounds that effectuate a reversible or irreversible colour change when a specific temperature threshold is crossed. A thermochromic pigment basically comprises three main components: (i) an electron donating colouring organic compound, (ii) an electron accepting compound and (iii) a solvent reaction medium determining the temperature of the colouring reaction to occur.

A thermochromic particulate material which may be used may be prepared from particles of a non-thermoplastic resin having enclosed therein the three components of electron-donating chromogenic substance, electron-accepting substance and solvent by coating the particles with a hydrophilic high-molecular-weight compound. The thermochromic particulate material, when incorporated into a vinyl chloride plastisol, remains free of the influence of the plasticizer, stabilizer, lubricant or the like contained in the plastisol and retains very high stability even when heated.

The process for preparing a molded product of thermochromic polyvinyl chloride is characterized by incorporating a thermochromic particulate material into a vinyl chloride plastisol comprising a vinyl chloride resin, plasticizer, stabilizer, lubricant and filler. Thereafter molding the resulting mixture. The thermochromic particulate material being prepared from particles of a non-thermoplastic resin having encapsulated therein the three components of electron-donating chromogenic substance, electron-accepting substance and solvent by coating the particles with a hydrophilic high-molecular-weight compound.

A molded thermochromic polyvinyl chloride material can thereby be prepared which reliably undergoes a reversible color change with a change of temperature. A material like this becomes skin-colored when the temperature rises beyond about 40° C. The color change is reversible. This is further described in U.S. Pat. No. 4,826,550.

Such thermochromic pigments and the mechanism bringing about the temperature triggered colour change to occur are well-known in the art and are for example described in U.S. Pat. No. 4,826,550 and U.S. Pat. No. 5,197,958.

Thermochromic or temperature sensitive colour changing fibres are known from the textile field to be used in clothing, sport equipment etc. The fibres are either produced by blending a thermochromic pigment in the base resin from which the fibres are to be produced, for example a polyolefin, such as polyethylene or polypropylene, polyester, polyvinyl alcohol etc. or by using a thermochromic colouring liquid for the fibers. The production of temperature sensitive colour-changing fibres are disclosed in for example JP2002138322 and JP2001123088. The fibres change colour at a selected temperature. The change of colour is either reversible or irreversible.

An example of a fiber which can be used is a thermochromic fiber which is partly characterized in that the flexural modulus of elasticity of a base resin is within the range of 300-1,500 MPa in the temperature-sensing color-changing fiber. The fiber is formed by melt blending a thermally color-changing pigment in a dispersed state in the base resin of a polyolefin resin and/or the polyolefin resin blended with a thermoplastic resin. This fiber is earlier used in the textile field. The inventors have found that fibers with this characteristics may also be suited for use in absorbent articles, especially diapers. The fiber is further described in JP 2002-138322.

In another embodiment the thermochromic fiber is a thermosensitive color-changing acrylic synthetic fiber. Such fibers may be constituted of a plurality of long fibers or short fibers of a thermosensitive color-changing synthetic acrylic fiber having 1-100 μm outer diameter of monofilament. The fibers may be formed by dispersing 0.5-40 wt. % of a thermosensitive pigment containing essential three ingredients of (A) an electron donating coloring organic compound, (B) an electron-accepting compound and (C) a reaction solvent determining the occurrence temperature of a coloring reaction of the ingredients A and B. This is describes in more detail in JP 2001-055623.

Another thermochromic fiber is a conjugate fiber which is excellent in reversible color changeability, brightness and durability. It may be produced by using a (1) thermal color changing polyester composed of a thermal color changing material-containing thermoplastic polyester and (2) a fiber-forming polyester in which ≥50 mol % of an acid component is terephthalic acid; 0-50 mol % thereof is isophthalic acid and ≥70 mol % of a diol component is composed of butanediol and/or hexanediol are subjected to melt conjugate spinning. The resultant yarn is then drawn to afford the objective fiber which is conjugate fiber, containing a part composed of the component (1) joined to a part composed of the component (2) and having ≥1.5 g/denier fiber strength, ≤80% fiber elongation and ≤25% shrinkage factor in boiling water. This is further described in JP 4241115.

Another fiber which is excellent in friction durability and mechanical characteristics which may be suitable for the invention can be achieved by using a low-melting thermoplastic resin containing a temperature-sensitive color changing granular substance as a core component and a high-melting thermoplastic resin as a sheath component at a specific ratio.

The fiber is obtained by mixing an acid developing substance (e.g. 3,3'-dimethoxyfluoran) with an acidic substance (e.g. phenol) and a solvent (e.g. octyl alcohol), granulating the resultant mixture and carrying out conjugate spinning of a thermoplastic resin (e.g. polypropylene), having ≤230° C. melting point and containing 1-40 wt. % resultant temperature-sensitive color changing granular substance. The granules having 1-50 μm grain diameter and ≥200° C. heat resistance as a core component and a thermoplastic resin (e.g. nylon) having ≤280° C. melting point as a sheath composition at (1/9)-(9/1) weight ratio of core component:sheath component, having a smooth surface and excellent in mechanical characteristics with a high level of temperature-sensitive color changing function. This method is further described in JP 3161511.

The temperature sensitive pigment used in the thermochromic fibers has preferably an average particle size of 0.5-50 μm, preferably 0.5-30.0, even more preferably μm 0.5-15.0 μm measured by appropriate ASTDM standard method.

The thermosensitive pigment may preferably be of a microcapsule type which is known in the art of thermosensitive pigments.

DESCRIPTION OF PREFERRED EMBODIMENTS

The absorbent article shown in FIG. 1 is in the form of a diaper 1 having a longitudinal, y, and a transverse direction, x, and comprises, as seen in its longitudinal direction, a front portion 2, a back portion 3 and a crotch portion 4 there between. In its most common form the diaper comprises an absorbent structure 5 and a cover enclosing the absorbent structure. Said cover comprises an inner liquid pervious cover 6 on the wearer facing side of the absorbent structure 5 and an outer liquid impervious cover 7 on the garment facing side of the absorbent structure. The outer cover may in one embodiment comprise a liquid impervious plastic film 7 and a nonwoven layer 15 on the garment facing side of the film. The inner liquid pervious cover 6 is often referred to as topsheet, while the outer liquid impervious cover 7 is often referred to as backsheet. An acquisition layer 8 is arranged between the inner liquid pervious cover 6 and the absorbent structure 5.

The inner cover 6 and the outer cover 7 extend outward beyond the peripheral edges of the absorbent structure 5 and have their inner surfaces bonded to each other, e.g. by gluing or welding by heat or ultrasonic. The inner and outer cover materials may further be bonded, e.g. by adhesive, to the absorbent structure.

The areas of the article adjacent the leg openings are along the longitudinal side edges provided with elastic members 9 which are bonded between the inner cover 6 and the outer cover 7 material layers in a stretched condition so as to provide elasticized leg openings of the diaper. Corresponding elastic members are arranged to extend in the transverse, x, direction in the front 2 and back portion 3 adjacent the transverse side edges forming the waist opening of the diaper.

The back portion 3 is provided with fasteners 10 attached thereto. The fasteners are intended to be fastened to the front region of the article to form a pant-like shape. The fasteners 10 may be in the form of adhesive tapes or hook elements adapted to attach to a loop material, for example in the form of a nonwoven material forming the outer coversheet of the diaper.

Figure 3:
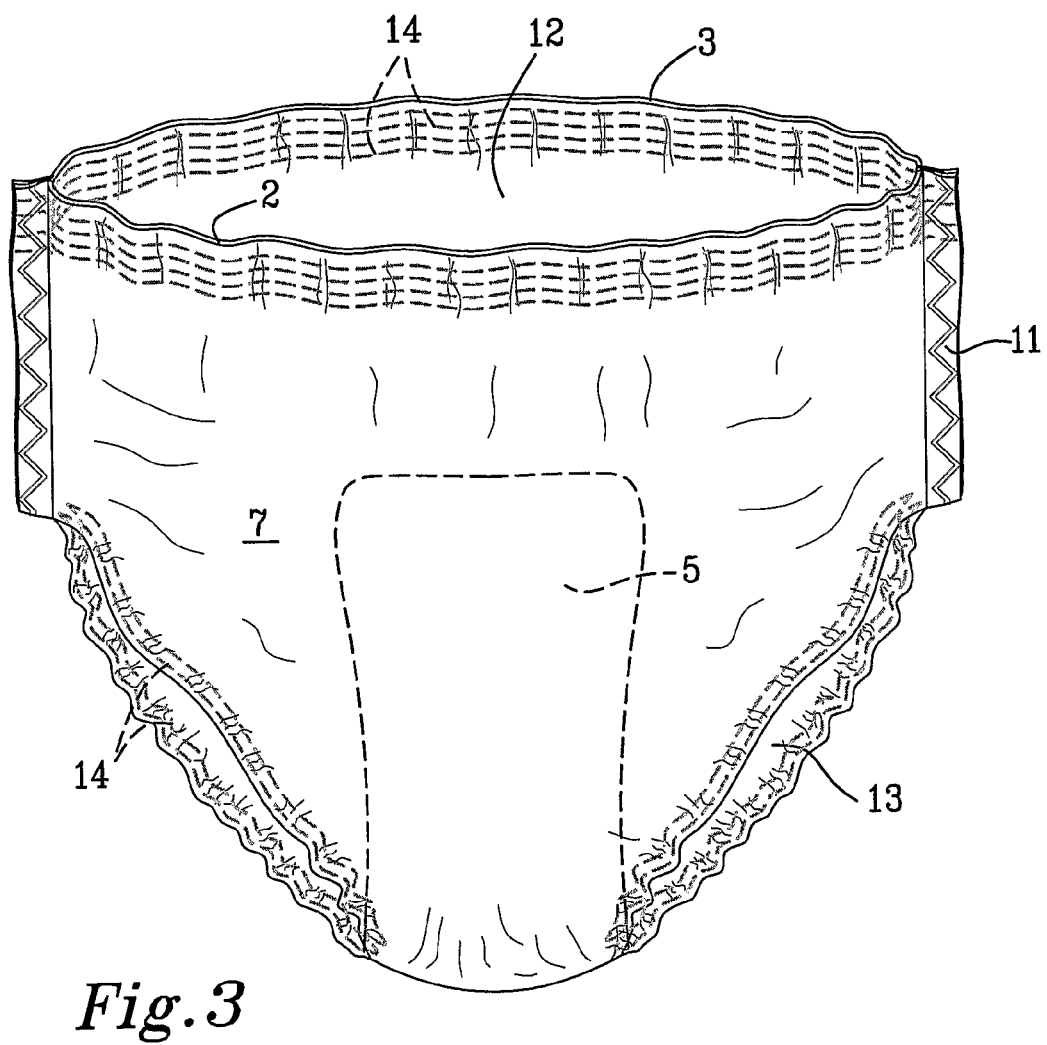
FIG. 3 is a schematic perspective view of a pant diaper.

FIG. 3 shows a so called pant diaper in which the front and back portions 2 and 3 are joined to each other along their longitudinal side edges thereof forming side seams 11, to define a waist-opening 12 and a pair of leg-openings 13. The front and back portions 2 and 3 are joined along said side seams 11, for example by adhesive, ultrasonic welding, heat sealing or the like. The front and back portions 2 and 3 may be joined along said side seams with the inner cover 6 facing inwards, as is shown in the drawings. Alternatively they are joined in an overlapped manner with the inner cover 6 of either the front or back portion facing the outer cover 7 of the opposite region.

In an alternative form the pant diaper comprises a core region comprising the absorbent structure, a liquid pervious inner cover and a liquid impervious outer cover as disclosed above, and a chassis region outside the core region, wherein the chassis region comprises a coversheet of a soft and comfortable material, for example an elastic laminate. An example of such a pant diaper is disclosed in PCT/SE2004/001004.

The waist area, at least a part of the leg opening area and the side areas adjacent the side seams 11 are elasticized. The elastification is usually accomplished by a plurality of elastic members, such as elastic threads 14, contractably affixed in a stretched condition between the outer cover 7 and the inner cover 6. Alternatively elastic materials, such as an elastic laminate, may be used to form the chassis of the article in those areas where elasticity is desired.

Figure 4:
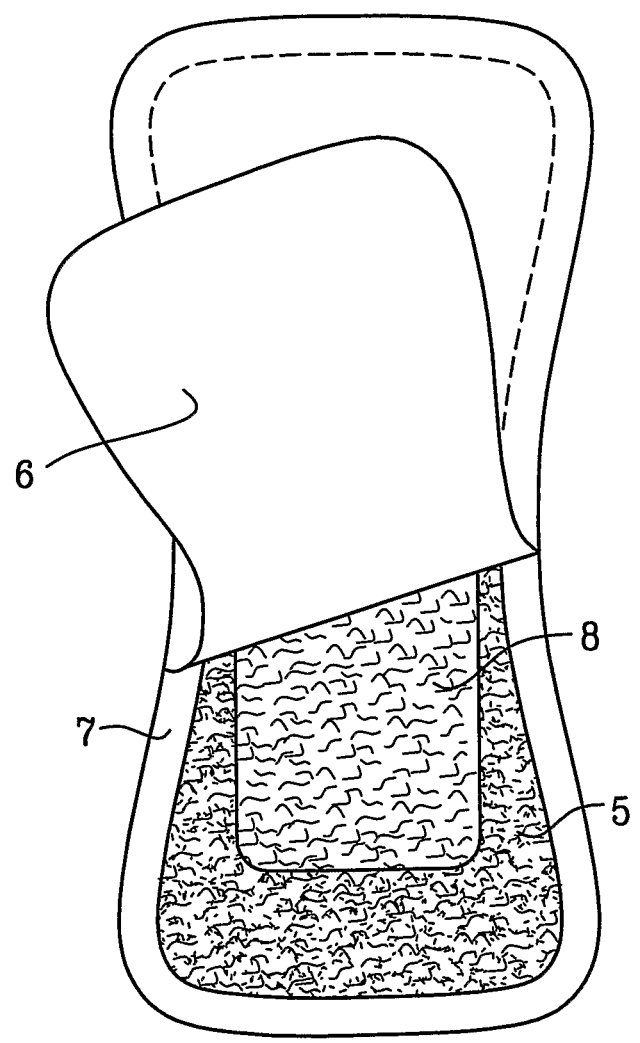
FIG. 4 is a schematic view of a sanitary napkin or incontinence guard.

FIG. 4 shows a further embodiment in the form of an incontinence guard or sanitary napkin intended to be worn in the panties of a wearer.

The absorbent articles shown in the drawings are only examples of some common types of personal care absorbent articles and the invention may be applied to any type of absorbent articles falling under the definition given above.

The absorbent article contains thermochromic fibres. As mentioned above thermochromic fibres are fibres having incorporated therein a thermochromic pigment. The thermochromic pigment basically comprises three main components. (i) an electron donating colouring organic compound, (ii) an electron accepting compound and (iii) a solvent reaction medium determining the temperature of the colouring reaction to occur.

Such thermochromic pigments and the mechanism bringing about the temperature triggered colour change to occur are well-known in the art and are for example described in U.S. Pat. No. 4,826,550 and U.S. Pat. No. 5,197,958. The first mentioned document discloses molded products of polyvinyl chloride, having incorporated therein thermochromic particulate material. The last mentioned document discloses a wetness indicating diaper having a thermochromic ink printed on the diaper backsheet.

A description of fibers having incorporated therein such thermochromic pigments can be found in any of the following Japanese published patent applications: JP 2002-138322 disclosing thermally colour-changing fibres for various textile applications, such a imitated wool; JP 2001-123088 disclosing a reversibly thermochromic colouring liquid for fibers and fabrics made therefrom; JP 2001-055623 disclosing thermosensitive colour-changing synthetic acrylic fibres; and JP 8027653 disclosing a thermally colour-changing nonwoven material containing a certain amount of reversibly colour-changing crimped fibres.

The thermochromic pigment may be incorporated in the base resin of the fibers in the form of microcapsules or as a colouring liquid for the fibres.

The entire fiber may be coloured by the thermochromic pigment, or the fiber may be of a bicomponent type, wherein either the core or the outer casing of the fiber is provided with the thermochromic pigment. The change of colour may either be reversible or irreversible.

The thermochromic fibers may, depending on the intended purpose of the thermochromic function, be incorporated in any suitable component of the absorbent article, such as the outer liquid impermeable cover, a layer arranged between the absorbent structure and the outer cover, the absorbent structure, a layer of an absorbent structure, the inner liquid pervious cover or the acquisition layer.

Thermochromic fibres having a change of colour at a temperature slightly below body temperature, or in the interval from about 30 to about 37° C., may be used as a wetness indicator indicating the presence of body fluid, when incorporated in for example the absorbent structure 5, the outer coversheet 7, 15, a layer arranged between the outer coversheet and the absorbent structure 5 or in the acquisition layer 8. They may also be incorporated in a nonwoven outer garment facing layer 15, outside a liquid impervious plastic film, of the outer coversheet, since the thin plastic film is normally sufficiently thermally conductive to allow the temperature to rise on the outer surface thereof when the article is wetted with body fluid.

They may further be used as a fever indicator, when incorporated in the inner coversheet 6, the acquisition layer 8 or the absorbent structure 5. In this case the thermochromic fibres should have a change of colour at an interval slightly above normal body temperature, or in the interval from about 37.5 to about 39° C.

Thermochromic fibres incorporated in the outer coversheet 7, 15 may also be used for amusement purposes and something for the baby to play with, such that when the baby puts his/her hand on the diaper an imprint of the hand in the form of different colour will occur for a while, but disappear again, in the case of reversible thermochromic fibers.

Thermochromic fibres may further be incorporated in an elastic material, for example an elastic laminate which in some parts has bee de-elastified by heat treatment, ultrasonic welding or the like. The elastic material may be an elastic nonwoven, a laminate of nonwoven and film or a nonwoven laminate. The thermochromic fibers in the de-elastified portions will change colour triggered by the heat treatment or ultrasonic welding, so as to indicate where de-elastification has occurred. The elastic laminate may form part of an absorbent article, for example elastic side panels of a diaper or pant diaper.

One further use of thermochromic fibers is as a function control of *Lactobacillus* or other microorganism incorporated in for example the inner coversheet 6, the acquisition layer 8 and/or the absorbent structure 5. This is done by indicating whether a certain temperature, above which the microorganism looses its function, has been exceeded during transport and storage. The thermochromic fibres should in this case change colour at a temperature of at least 40° C., preferably at least 50° C. The change of colour of the thermochromic fibres should in this case be irreversible.

The thermochromic fibers may be incorporated substantially homogeneously in an entire layer and mixed with other fibers in the layer. Alternatively they are inhomogeneously incorporated only in parts of a layer. A further alternative is that a separate fibrous layer, for example a nonwoven layer, produced mainly (at least 50%) or even entirely from thermochromic fibres as the sole fibrous component is incorporated in the article. An appropriate amount of the thermochromic fibres in for example an inner coversheet, an acquisition layer, an absorbent structure or a layer in an absorbent structure or an outer coversheet, is at least 1% by weight, preferably at least 5%, more preferably at least 10% by weight and most preferably from 20 to 70% by weight based on the weight of said fibrous layer in areas in which said thermochromic fibres are distributed. Thus if the thermochromic fibres are distributed in only half of the layer, the weight-% should be based on the weight of that half part of the layer.

The rest of the fibres, with which the thermochromic fibres are mixed, may vary depending on which component of the absorbent article the thermochromic fibres are incorporated in, if it for example is a backsheet material, a coversheet, a backsheet or an absorbent structure. Thus the rest of the fibres may be cellulosic fibres, polyethylene, polyproplyene, polyester, polylactide, viscose fibres and the like.

In one embodiment the rest of the fibres with which the thermochromic fibres are mixed are made of the same polymeric material as the thermochromic fibres. Thus if the thermochromic fibres comprises polypropylene having a thermochromic pigment incorporated therein, these thermochromic fibres may be mixed with other polypropylene fibres with no thermochromic pigment in them.

In case a fibrous layer consisting of thermochromic fibres as the sole fibrous component is used, such layer should have a basis weight of at least 7, preferably at least 10 and more preferably at least 15 g/m$^2$.

Two or more types of thermochromic fibres may be used in the same article. These different thermochromic fibres may have different colours and/or different trigger temperatures.

The time it takes for the colour change to occur may at least for some applications be of importance. For example it may be desired that the change of temperature occurs in less than 3 seconds, preferably in less than 2 seconds and more preferably in less than 1 second from when the fibres have been exerted to the trigger temperature. A high impact temperature (high above the trigger temperature) on the thermochromic fibres will give a faster colour change than a low impact temperature (close to the trigger temperature).

It is pointed out that the present invention is not limited to the embodiments described above and shown in the drawings, but that a plurality of modifications are possible within the scope of the claims and equivalents thereof.

The invention claimed is:

1. An absorbent article comprising an absorbent structure, a liquid impervious outer coversheet and a nonwoven layer arranged between the outer coversheet and the absorbent structure, wherein said layer comprises thermochromic fibres, in which a thermochromic pigment is blended with a resin from which the fibers are produced.

2. The absorbent article as claimed in claim 1, wherein said layer comprises a fibrous layer containing at least 1% by weight of said thermochromic fibres, based on the weight of said fibrous layer in areas in which said thermochromic fibres are distributed.

3. The absorbent article as claimed in claim 1, wherein said layer comprises a fibrous layer having a basis weight of at least 7 g/m$^2$, and containing the thermochromic fibres as the sole fibrous component.

4. The absorbent article as claimed in claim 1, wherein the thermochromic fibers change colour at a temperature of between 25 and 40° C.

5. The absorbent article as claimed in claim 1, wherein said article comprises at least two different types of thermochromic fibers having different colours or different trigger temperatures.

6. An absorbent article comprising a liquid pervious inner coversheet, an absorbent structure, a liquid impervious outer coversheet and a liquid acquisition layer placed between the inner coversheet and the absorbent structure, wherein said absorbent structure contains a fibrous nonwoven layer containing thermochromic fibres as the sole fibrous component.

7. The absorbent article as claimed in claim 6, wherein the absorbent structure comprises at least 1% by weight of said thermochromic fibres, based on the weight of said fibrous layer.

8. The absorbent article as claimed in claim 7, wherein said fibrous layer having a basis weight of at least 7 g/m$^2$.

9. The absorbent article as claimed in claim 6, wherein the thermochromic fibers change colour at a temperature of between 25 and 40° C.

10. The absorbent article as claimed in claim 6, wherein said article comprises at least two different types of thermochromic fibers having different colours or different trigger temperatures.

11. The absorbent article as claimed in claim 6, wherein the absorbent structure is not monolithic with the liquid acquisition layer.

12. A method of indicating wetness in an absorbent article, the method comprising:
    blending a thermochromic pigment with a resin to produce a plurality of thermochromic fibers; and
    including the thermochromic fibers in the absorbent article,
    wherein: (i) the absorbent article comprises an absorbent structure, a liquid impervious outer coversheet and a nonwoven layer arranged between the outer coversheet and the absorbent structure, wherein said layer comprises the thermochromic fibres; or (ii) the absorbent article comprises a liquid pervious inner coversheet, an absorbent structure, a liquid impervious outer coversheet and a liquid acquisition layer placed between the inner coversheet and the absorbent structure, wherein said absorbent structure comprises the thermochromic fibres.

13. The method of claim 12, further comprising creating colour imprints of hands in the absorbent article to enhance customer product perception.

14. A method of indicating a fever in a wearer of an absorbent article, the method comprising:
    blending a thermochromic pigment with a resin to produce a plurality of thermochromic fibers; and
    including the thermochromic fibers in the absorbent article,
    wherein: (i) the absorbent article comprises an absorbent structure, a liquid impervious outer coversheet and a nonwoven layer arranged between the outer coversheet and the absorbent structure, wherein said layer comprises the thermochromic fibres; or (ii) the absorbent article comprises a liquid pervious inner coversheet, an absorbent structure, a liquid impervious outer coversheet and a liquid acquisition layer placed between the inner coversheet and the absorbent structure, wherein said absorbent structure comprises the thermochromic fibres.

15. A method of controlling microorganisms in an absorbent article, the method comprising:
    blending a thermochromic pigment with a resin to produce a plurality of thermochromic fibers; and including the thermochromic fibers in the absorbent article, wherein: (i) the absorbent article comprises an absorbent structure, a liquid impervious outer coversheet and a nonwoven layer arranged between the outer coversheet and the absorbent structure, wherein said layer comprises the thermochromic fibres; or (ii) the absorbent article comprises a liquid pervious inner coversheet, an absorbent structure, a liquid impervious outer coversheet and a liquid acquisition layer placed between the inner coversheet and the absorbent structure, wherein said absorbent structure comprises the thermochromic fibres.

16. A method of indicating de-elastification of a portion of an absorbent article, the method comprising:

blending a thermochromic pigment with a resin to produce a plurality of thermochromic fibers; and including the thermochromic fibers in the absorbent article, wherein: (i) the absorbent article comprises an absorbent structure, a liquid impervious outer coversheet and a nonwoven layer arranged between the outer coversheet and the absorbent structure, wherein said layer comprises the thermochromic fibres; or (ii) the absorbent article comprises a liquid pervious inner coversheet, an absorbent structure, a liquid impervious outer coversheet and a liquid acquisition layer placed between the inner coversheet and the absorbent structure, wherein said absorbent structure comprises the thermochromic fibres.

* * * * *